United States Patent
Gregory (10) Patent No.: US 6,660,001 B2
(45) Date of Patent: Dec. 9, 2003

(54) MYOCARDIAL REVASCULARIZATION-OPTICAL REFLECTANCE CATHETER AND METHOD

(75) Inventor: Kenton W. Gregory, 3737 SW. Council Crest Dr., Portland, OR (US) 97201

(73) Assignees: Providence Health System-Oregon, Seattle, WA (US); Kenton W. Gregory, Portland, OR (US)

( * ) Notice: Subject to any disclaimer, the term of this patent is extended or adjusted under 35 U.S.C. 154(b) by 190 days.

(21) Appl. No.: 09/765,968

(22) Filed: Jan. 19, 2001

(65) Prior Publication Data

US 2001/0027316 A1 Oct. 4, 2001

Related U.S. Application Data

(60) Provisional application No. 60/177,323, filed on Jan. 21, 2000.

(51) Int. Cl.[7] .............................................. A61B 18/18
(52) U.S. Cl. ................. 606/15; 606/7; 606/10; 606/12; 606/41; 607/88; 607/101; 607/122; 604/20; 604/22; 356/3.1; 356/4.1; 367/99; 367/103
(58) Field of Search ................................. 606/7, 10–16, 606/41; 607/2, 3, 5–8, 122, 88, 89, 100–102; 128/898; 604/20, 21, 22; 367/99, 103, 104; 356/3.1, 4.07, 4.09, 5.01–5.03

(56) References Cited

U.S. PATENT DOCUMENTS

| | | | | |
|---|---|---|---|---|
| 5,252,839 A | | 10/1993 | Fouquet ........................ 257/13 |
| 5,350,377 A | * | 9/1994 | Winston et al. ................ 606/15 |
| 5,391,199 A | * | 2/1995 | Ben-Haim .................. 607/122 |
| 5,425,367 A | * | 6/1995 | Shapiro et al. ........... 128/653.1 |
| 5,725,521 A | | 3/1998 | Mueller .......................... 17/36 |
| 5,752,518 A | * | 5/1998 | McGee et al. ......... 128/662.06 |
| 5,813,403 A | * | 9/1998 | Soller et al. ................. 128/633 |
| 5,848,969 A | * | 12/1998 | Panescu et al. ............. 600/462 |
| 5,893,848 A | * | 4/1999 | Negus et al. .................. 606/41 |
| 5,968,059 A | | 10/1999 | Ellis et al. ...................... 17/32 |
| 6,001,091 A | | 12/1999 | Murphy-Chutorian et al. . 17/36 |
| 6,024,703 A | * | 2/2000 | Zanelli et al. ............... 600/437 |
| 6,030,380 A | | 2/2000 | Auth et al. ..................... 17/30 |
| 6,053,911 A | * | 4/2000 | Ryan et al. .................... 606/33 |
| 6,056,742 A | | 5/2000 | Murphy-Chutorian et al. . 17/36 |
| 6,086,534 A | * | 7/2000 | Kesten ........................ 600/439 |
| 6,117,128 A | * | 9/2000 | Gregory ......................... 606/7 |
| 6,447,504 B1 | * | 9/2002 | Ben-Haim et al. ............. 606/15 |

OTHER PUBLICATIONS

Puliafito et al. "Optical Coherence Tomography of Ocular Diseases" Slack Inc.:1996, Chapter 1, pp. 3–8.*
Huang et al., "Optical Coherence Tomography," *Science*, vol. 254, pp. 1178–1181 (1991).
Puliafito et al., *Optical Coherence Tomography of Ocular Diseases*, Slack, Inc. Chapter 1 (pp. 3–8), and Appendix (pp. 369–374) 1996.

* cited by examiner

*Primary Examiner*—Michael Peffley
*Assistant Examiner*—Ahmed Farah
(74) *Attorney, Agent, or Firm*—Marger Johnson & McCollom, PC (57) ABSTRACT

A myocardial revascularization device has a catheter suitable for use in a myocardial revascularization procedure, the catheter including an elongate body having a proximal end and a distal end, and tissue-ablating means housed at least partially within the catheter and capable of effectuating tissue ablation adjacent the distal end of the catheter. The device further has an optical reflectance fiber housed within the catheter and coupled to an optical reflectance system. The device is operative to transmit a reflectance signal in the optical reflectance fiber, the reflectance signal including either short optical pulses or low-coherence light. The optical reflectance system is operative to gauge tissue ablation, measure a thickness of tissue adjacent the catheter, and/or determine a position of the distal end relative to adjacent tissue using either of optical time-domain reflectance or optical coherence interferometry.

16 Claims, 10 Drawing Sheets

MYOCARDIAL REVASCULARIZATION-OPTICAL REFLECTANCE CATHETER AND METHOD

CROSS REFERENCE TO RELATED APPLICATIONS

This application claims priority from U.S. Provisional Application Ser. No. 60/177,323, filed on Jan. 21, 2000, which is incorporated by reference.

BACKGROUND OF THE INVENTION

The present invention relates to the field of transmyocardial revascularization (TMR), and more particularly, to an improved device and method for optically guiding the process of laser ablation in creating the revascularization channels. Channels are ablated to a proper depth and safety is enhanced by preventing complete perforation of the heart wall, where a fiber-optic or other waveguide can be precisely positioned adjacent an area to be laser-ablated, including at positions adjacent the posterior epicardial or endocardial surfaces of the heart and at trans-septal positions within the chambers of the heart.

Transmyocardial laser revascularization (TMR) is a procedure whereby laser channels are created in the walls of the heart to reduce angina in patients with ischemic coronary artery disease. This procedure is generally used with patients in whom no other revascularization procedure is possible or as an adjunct to other revascularization procedures involving repair or replacement of the epicardial coronary arteries, such as coronary artery bypass surgery or catheter-based angioplasty procedures.

Laser channels are created in the ischemic zones, initially by using direct exposure of the heart through cardiac surgery procedures. Once the heart is exposed, a laser energy delivery device is then placed against the outer surface of the heart and a channel ablated through the heart wall to the inner blood chamber of the heart. This surgical procedure has been effective in clinical trials; however, a non-surgical or less invasive procedure is desired.

Laser catheters were developed so that laser energy could be delivered from inside the left ventricle by passing one or more optical fiber-based devices from a femoral artery cannulation to the left ventricle, usually with fluoroscopic guidance. Catheter-based myocardial revascularization suffers from the possibility of epicardium perforation and consequent uncontrollable bleeding, potentially resulting in cardiac tamponade or coronary artery perforation, causing death in some cases.

Devices such as the NOGA Cardiac Navigation System (Biosense Webster, Inc., Diamond Bar, Calif.) have been used to help guide the laser catheter to the desired location in the left ventricle of the heart. The NOGA device uses a location sensor and electrodes incorporated into a catheter. The device acquires and records intra-cardiac electrical activation and ventricular motion in real-time for each acquired point, the data being used to provide a 3-D dynamic reconstruction of the heart chamber during a cardiac cycle. While useful to spatially locate the distal laser tip within the heart, devices of this sort provide no gauge of the depth of the laser channel created or of the proximity of the laser catheter to the epicardium. Channel depth and proximity to the epicardium are highly predictive of a possible and unwanted perforation. In a recently reported study, the Biosense device was used to guide percutaneous catheter based placement of laser channels. Because there was a fear of perforation of the myocardium and attendant serious complications, and no means of gauging either the channel depth or the distance of the tip of the laser catheter to the outside wall of the heart-the epicardium, clinical investigators were only allowed to use two pulses of laser energy. While this strategy proved to be safe, two laser pulses are not enough to create laser channels effectively. The results of the study showed that the therapy was safe, but there was no therapeutic effect compared to placebo. In fact, two laser pulses only make small indentations on the inside of the heart; no transmyocardial channels (the therapeutic goal) are created.

U.S. Pat. No. 5,893,848 to Negus et al. describes a gauging system using either a mechanical force transducer or an optical or ultrasound pulse emitter and transducer to detect time differences between reflections from the terminus of a channel and from the heart walls. The embodiment of the Negus device utilizing an optical sensor device senses the propagatable ablation energy as it is reflected by a tissue boundary. This embodiment requires an optical ablating energy source, e.g., laser or ultrasound, to measure distance. The potential problem of this sound-wave device in use is that bubbles, produced as an obligate consequence of vaporization of myocardium in creating the laser ablation, will interfere with the ultrasound signal. Ultrasound is highly reflected by gas; thus, the base of the laser channel will be obscured by bubbles during real-time image or signal acquisition. This device is therefore an ineffective means by which to monitor the progress of laser ablation.

While guided laser channels are potentially superior to laser channels being directed by fluoroscopy, clinical trials of the former have shown perforations.

Secondly, it is not known how deep the channels should be and there is currently no effective manner to determine the depth of the channel aside from fluoroscopy.

Randomized clinical trials of open surgical transmyocardial laser revascularization have consistently shown statistically significant efficacious results in reducing patients' angina and this technology is now FDA-approved. Catheter based trials of laser revascularization have failed to show significant improvement in patient angina. The only prominent difference between the two therapies (aside from a thoracotomy, which has not been shown to reduce angina) has been that the catheter-based therapies do not create transmyocardial channels. Rather, they produce a shallow channel, always less that 5 mm in depth and in most cases 2 mm or less. Assuming that the therapeutic effect is conferred by the channels created, shallow channels appear to be sub-therapeutic.

Channel depths created by percutaneous catheter approaches have been limited, due to safety concerns and the absolute need to avoid perforating the myocardium. In an open-chest surgical procedure, channels that bleed can be monitored and/or sutured shut. Conversely, a left ventricular perforation occurring during a percutaneous catheter-based procedure can cause uncontrolled bleeding and rapid onset of cardiac tamponade which can progress rapidly to shock and death. The only therapy is to place a needle in the chest and remove the pericardial blood which then allows effective cardiac function, but bleeding can continue and may require open-heart surgery.

Accordingly, a need remains for a better way to gauge and control myocardial revascularization.

SUMMARY OF THE INVENTION

The present invention overcomes these problems and limitations of the prior art by combining myocardial revascularization with optical reflectance.

Optical coherence reflectance (OCR) (or optical coherence tomography, OCT) is a structure-imaging method using detection of light reflectance signals. Heretofore, the technique has been used primarily to image blood vessels and structures of the eye. OCT uses infrared light to acquire cross-sectional images of tissue on the micrometer scale. OCT uses low-coherence interferometry to produce a two- or three-dimensional image of optical scattering from internal tissue microstructures in a way that is analogous to ultrasonic pulse-echo imaging. The images are taken using near-infrared light, avoiding the dangers associated with ionizing radiation, as with x-ray images.

Near-infrared light penetrates deeply into tissue, making it useful for imaging of internal structure. The majority of the transmitted light is highly scattered as it penetrates into the tissue. Scattered photons dominate in most imaging applications, leading to blurred images. By using a white light Michelson interferometer as a gate, OCT detects only the unscattered photons, thus generating high-resolution images. Further, heterodyning techniques are used to detect very low levels of reflected light from tissue. OCR can detect reflected signals as small as approximately $1 \times 10^{-9}$ of the incident optical power.

Because the frequency or wavelength of light is so much shorter than that of ultrasound-mediated imaging technologies, the resolution can be an order of magnitude better. Increased resolution is important, given the scale of the tissues involved in the heart. The resolution of ultrasound is at best approximately 100 microns, whereas OCR can achieve resolutions of approximately 5 microns. This increase translates into increased safety when the operator or surgeon is trying to precisely position a catheter close to the epicardium or avoid perforation while ablating or removing myocardial tissue.

OCT is described in further detail in *Optical Coherence Tomography of Ocular Diseases*, (C. A. Puliafito et al., SLACK, Inc.: 1996), incorporated by reference. See in particular chapter 1, pp. 3–8 and Appendix, pp. 369–374).

Because OCR data and OCT images are based on the optical backscattering properties of tissue, changes in tissue composition or structure are detectable using this technique.

One aspect of the present invention is a myocardial revascularization device, comprising a catheter suitable for use in a myocardial revascularization procedure, the catheter comprising an elongate body having a proximal end and a distal end; tissue-ablating means housed at least partially within the catheter and capable of effectuating tissue ablation adjacent the distal end of the catheter; and an optical reflectance fiber housed within the catheter, said fiber coupled to an optical reflectance system. The device is operative during a myocardial revascularization treatment to gauge tissue ablation by transmitting a reflectance signal in the reflectance fiber, the reflectance signal comprising either short optical pulses or low-coherence light. The device thereby gauges tissue ablation by means of time-domain reflectance or optical coherence reflectance.

In a preferred embodiment according to the present invention, the tissue-ablating means is laser energy transmitted by an optic fiber, housed at least partially within the catheter, to a tissue ablation site adjacent the distal end of the catheter.

Another aspect of the present invention is a method of measuring a thickness of a candidate tissue during a percutaneous myocardial revascularization procedure using a myocardial revascularization catheter, comprising positioning a distal end of the catheter adjacent the candidate tissue; and measuring the thickness of the candidate tissue using either of time-domain reflectance or optical coherence interferometry.

Another embodiment of the present invention is a method of determining a position of a myocardial revascularization catheter relative to a boundary of a subject tissue in a myocardial revascularization procedure, comprising positioning a distal end of the myocardial revascularization catheter adjacent to the subject tissue; ablating tissue; and locating the distal end of the catheter relative to the boundary of the subject tissue using either of time-domain reflectance or optical coherence interferometry.

The invention will become more readily apparent from the following Detailed Description, which proceeds with reference to the drawings, in which:

BRIEF DESCRIPTION OF THE DRAWINGS

FIGS. 1A–1C show two embodiments of a device according to the present invention:

DETAILED DESCRIPTION

The present invention improves catheter-based myocardial revascularization by using optical reflectance for guiding, locating or measuring the revascularization treatment. Optical reflectance provides a practical means of determining the thickness remaining in the left ventricular wall and can provide an operator with a signal when either perforation is impending or when the depth of the channel created is optimum for the revascularization effect.

A myocardial revascularization-optical reflectance (MR-OR) catheter of the present invention enjoys higher resolution guidance than is provided by current systems. Optical detection can be performed through a separate fiber or, with a beam splitter, through an ablating optical fiber to obtain reflectance signals from the treatment site. The signals are of sufficient resolution and intensity to determine the proximity of the laser tip from the epicardial surface, thus enabling the device to provide a laser ablation termination signal to the operator. Alternatively, the MR-OR catheter can be used to measure the remaining thickness of the tissue. This measurement can be used to gauge when to halt ablation of a channel where further tissue ablation could result in perforation of the tissue.

Figure 1A:
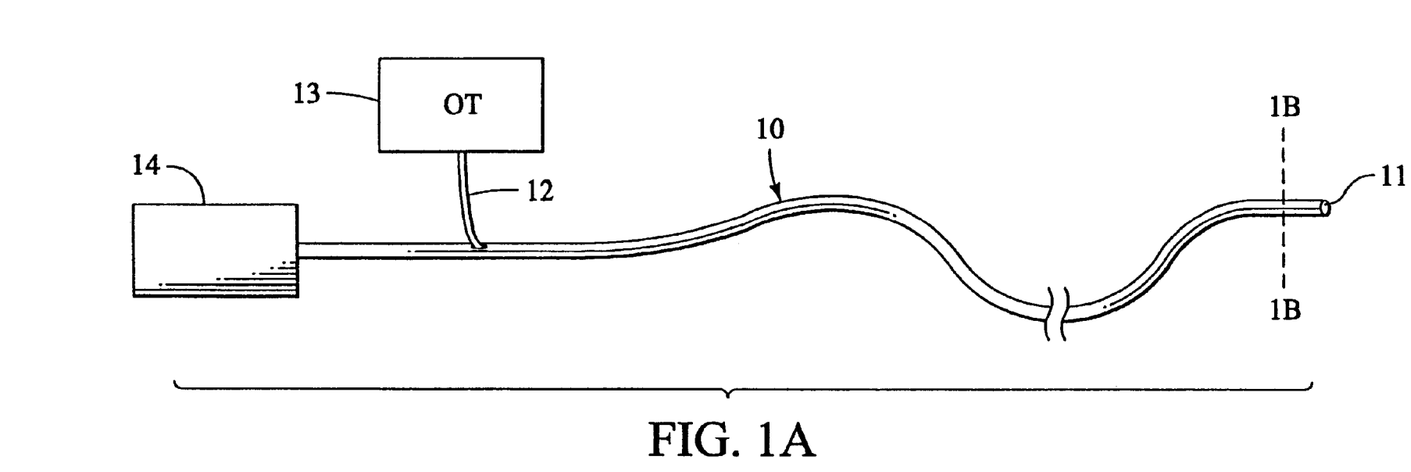
FIG. 1A is a diagram of a myocardial revascularization catheter device according to the present invention.

In one embodiment according to the present invention and shown in FIG. 1A, a MR-OR catheter 10 having an elongate body with proximal and distal ends. Arranged substantially within the catheter 10 are an optical reflectance fiber 12 for carrying reflectance signals, and tissue-ablating means 14 including an energy guide 16 housed at least partially within the catheter 10 and capable of effectuating tissue ablation adjacent a distal end 11 of the catheter 10. The reflectance fiber 12 is coupled to an optical reflectance system 13, such that the device is operative to gauge tissue ablation by transmitting a reflectance signal in the reflectance fiber 12 and wherein the reflectance signal comprises either short optical pulses or low-coherence light.

Figure 1B:
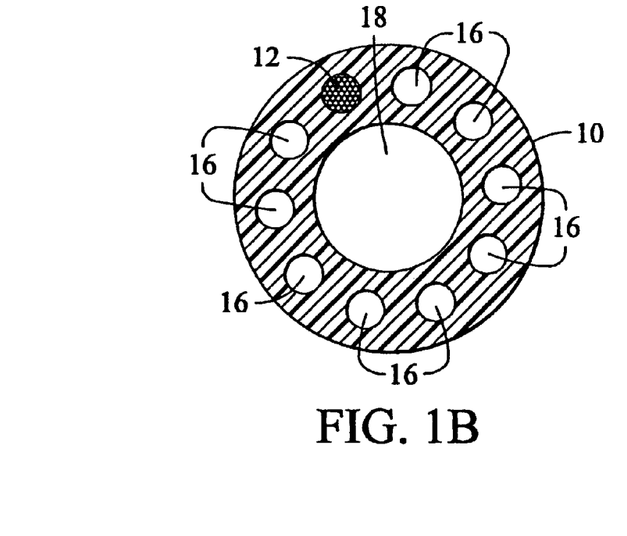
FIG. 1B shows a cross-section of one embodiment of the device taken through line 1B—1B in FIG. 1A.
Figure 1C:
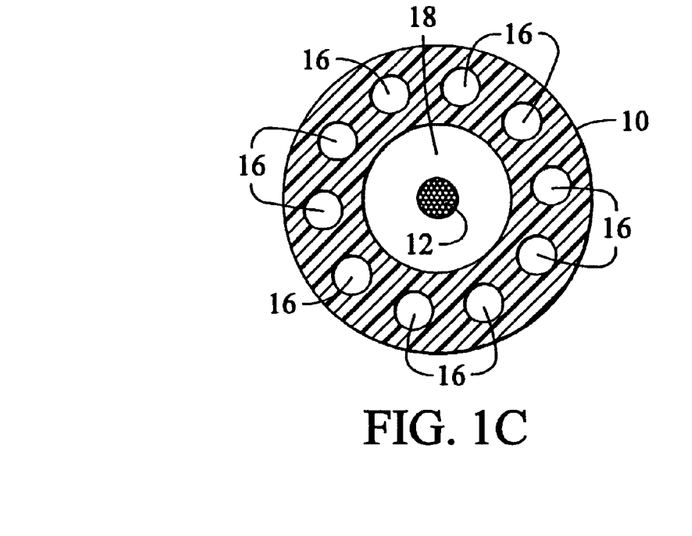
FIG. 1C shows a cross-section of an alternative embodiment of the device taken through line 1B—1B in FIG. 1A.

In the exemplary embodiment shown in FIGS. 1A–1C, the tissue-ablating means 14 comprises a laser-energy generating source coupled by a plurality of optic fibers 16, composed of fused silica optical fibers for transmitting laser energy, to the distal end 11 of the catheter 10. Suitable laser catheters are available from a number of manufacturers, e.g., a 1.7 mm Spectranetics laser catheter (Spectranetics, Inc., Colorado Springs, Colo.) connected to a Spectranetics excimer laser. This system is FDA-approved for use in laser angioplasty.

In the embodiment described, the optic fibers 16 and the reflectance fiber 12 are housed within substantially the length of the laser catheter 10. FIG. 1B shows a magnified view of a cross-section through the catheter device of FIG. 1A, taken through the line 1B—1B. In this embodiment, a plurality of optic fibers 16 has been arranged circumferentially around the central lumen 18 embedded in the catheter wall, with one of the plurality of optic fibers or bundles 12 coupled to the reflectance system 13 acting to transmit reflectance signals and the remainder of fibers 16 coupled to the laser-energy generating source 14 for transmission of laser energy. In one alternative embodiment, shown in the magnified cross-section view of FIG. 1C, the reflectance fiber or bundle 12 can be removably placed in the central lumen 18 normally used for a coronary angioplasty guidewire. The reflectance fiber 12 can be advanced through the lumen 18 and beyond the distal end 11 of the laser catheter 10, if needed.

While the described embodiments utilize optic fibers as part of the tissue-ablating means, the catheter of the present invention need not be limited to laser tissue-ablating means. Other devices, such as electrical or mechanical means, can be used in the catheter constructs described herein.

Moreover, alternative or more preferable fabrication strategies may be employed, and other physical arrangements of the catheter elements are possible. In another arrangement, the reflectance fiber 12 can be positioned as in FIG. 1B, with the tissue-ablating means 14 removably housed in the internal lumen 18 of the catheter 10. As another example, the catheter 10 can be a dual-lumen catheter. The tissue-ablating means 14 can be housed in one lumen and the reflectance fiber 12 housed in the other lumen. Alternatively, the reflectance fiber 12 and the tissue-ablating means 14 can reside in one lumen, with the other lumen available for other purposes. A saline or other irrigating flush can be introduced via lumen 18 to reduce the chance of ablated tissue attaching to the tip of the reflectance fiber 12 and thus obscuring signal acquisition.

The optical reflectance system preferably includes a low-coherence light source comprising a super-luminescent light-emitting diode. In embodiments having a super-luminescent light-emitting diode, the light produced thereby preferably has a wavelength in the range of 900 nm to 1400 nm.

Figure 2:
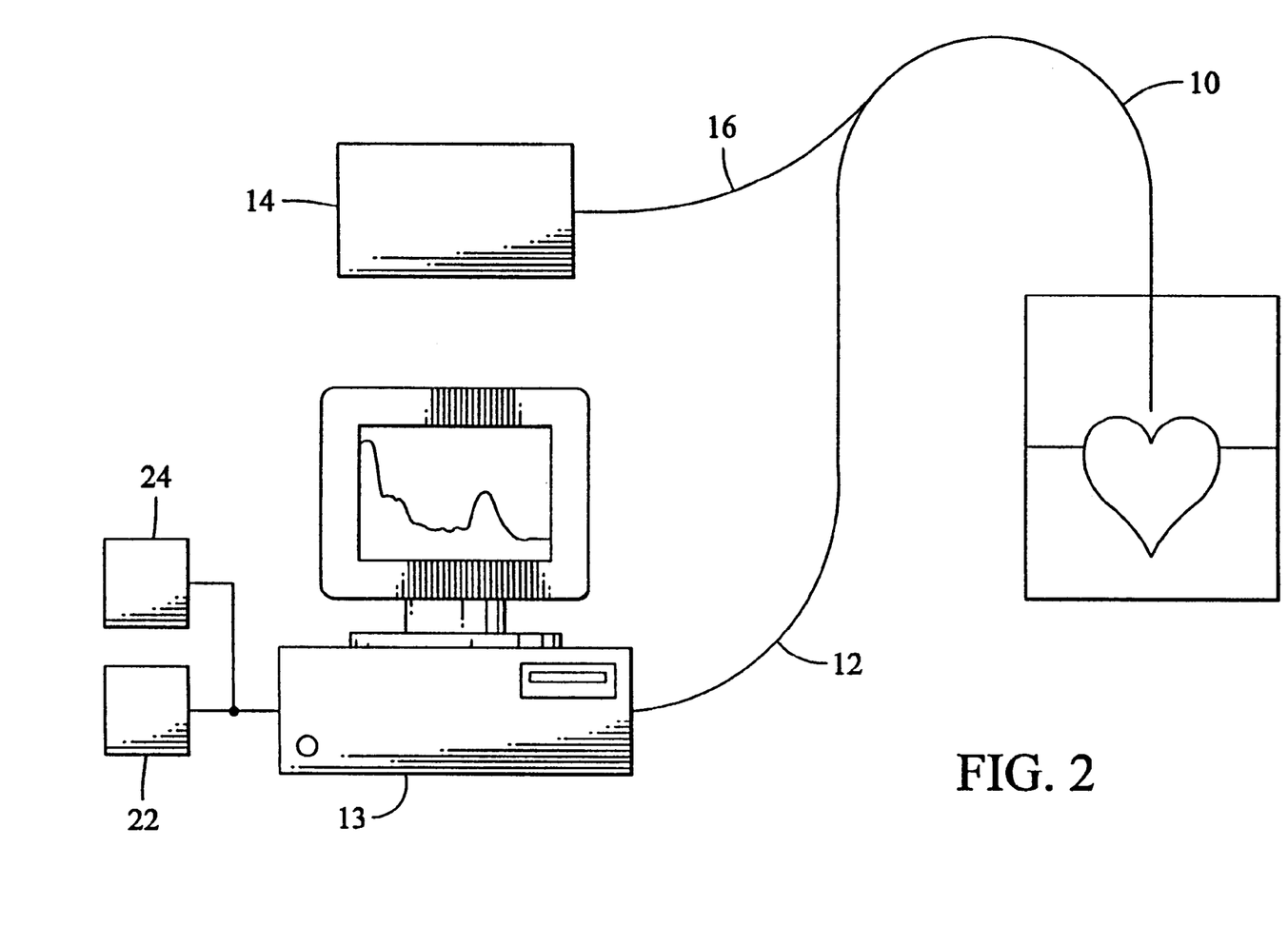
FIG. 2 is a block diagram of the system components as coupled in a myocardial revascularization procedure according to the present invention.

FIG. 2 shows the components used in a myocardial laser revascularization (MLR) procedure using the device of the present invention. Using the preferred embodiment of FIG. 1A to illustrate, the components comprise a MR-OR laser catheter 10 coupled to a laser energy-generating source by an optic fiber 16 within the laser catheter 10. A reflectance fiber 12 is coupled to a tissue imaging optical reflectance system 13. This optical reflectance system 13 is preferably an optical coherence reflectance system but can alternatively be a time domain reflectance system.

The embodiment shown in FIG. 2 has a tissue-ablating laser 14 and an optical fiber 16 coupled through catheter 10 to a site in a heart. The tissue-ablating laser 14 is preferably an excimer laser producing laser energy of wavelength approximately 308 nm.

Representative laser energy deployment is 25 Hz and 50 mJ/mm2, preferably in 125–200 ns pulses. As the laser energy is pulsed, the laser energy pulses and reflectance signals transmitted by the optical reflectance system are interleaved. In another embodiment, laser energy and reflectance signals can be transmitted concurrently using different wavelengths and filtering to separate reflectance signals from reflections of the laser energy.

The optical reflectance system 13 of one embodiment according to the present invention is an optical coherence reflectance (OCR) system, widely commercially available. Devices according to the present invention have employed an optical coherence reflectometry system (IntraLuminal Therapeutics, Inc., Carlsbad, Calif.). This system generates optical signals of wavelength 1310 nm (+30/−50 nm) launched into a 2.75 m reflectance fiber 12 housed within a catheter 10, described above. Reflected optical signals are returned through the reflectance fiber 12 to the OCR system 13 and converted into waveform data for display to an operator.

The device can alternatively, or additionally, comprise signaling means 22 for signaling an operator. The signaling means can be employed when a thickness of a tissue adjacent the distal end of the catheter is equal to or less than a tissue thickness selected prior to or contemporaneous with the revascularization procedure. Alternatively, the signaling means can be activated when a distance from the distal end of the catheter to an adjacent tissue boundary is equal to or less than the selected distance. It is readily apparent that the tissue-ablating means need not be limited to laser energy transmission, and that the signaling means can be used irrespective of the form of tissue ablation incorporated into the device.

Additionally, the device can comprise a disabling means 24 for disabling the tissue-ablating means. Similar to signaling means employment, the disabling means can be utilized when a thickness of a tissue adjacent the distal end of the catheter or a distance from the distal end of the catheter to an adjacent tissue boundary is equal to or less than a selected tissue thickness or selected distance, respectively. The disabling means is actuated independently of the tissue-ablating means, enabling its use with optical, mechanical or electrical tissue-ablating means.

Figure 3A:
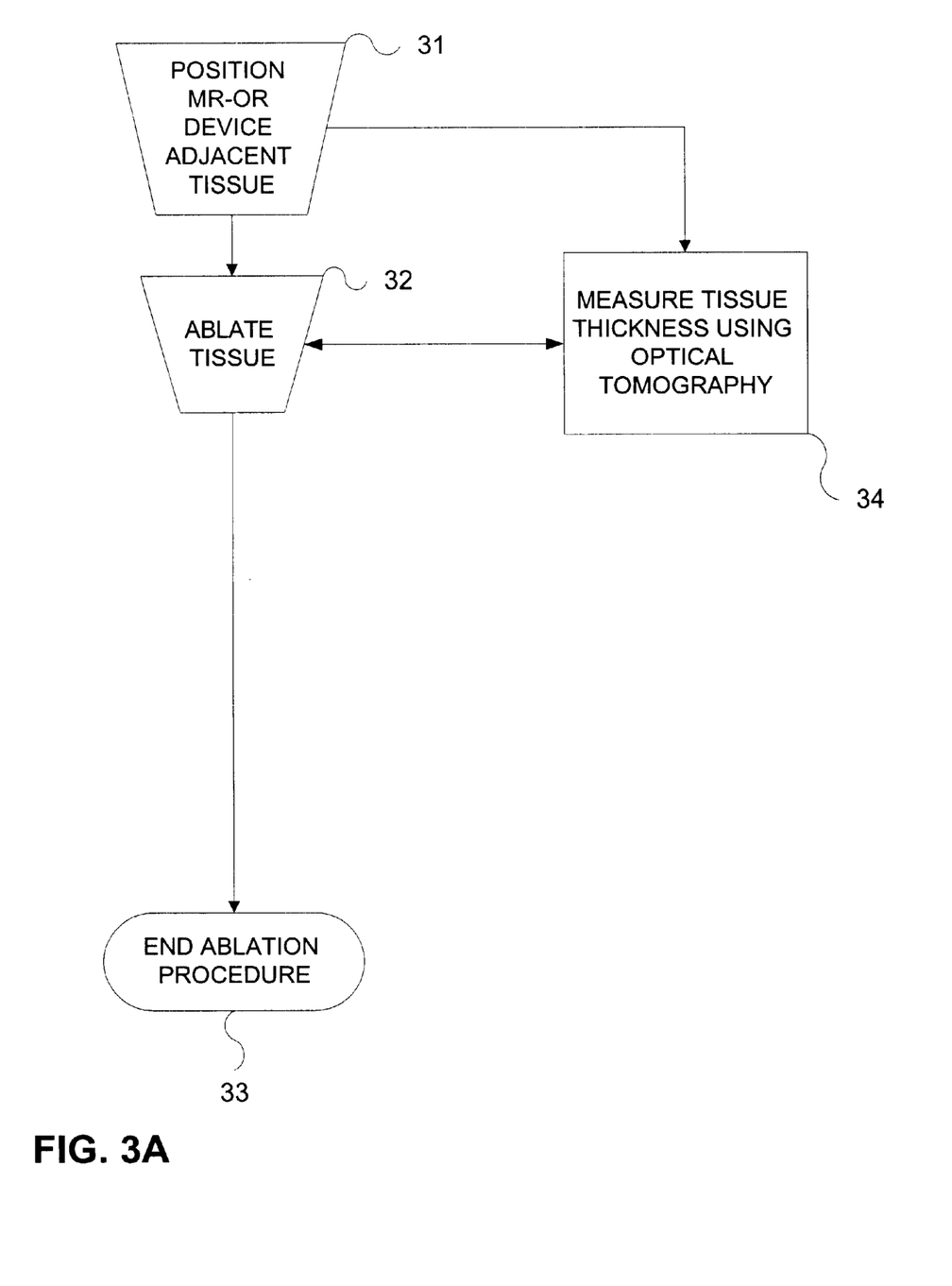
FIG. 3A is a flowchart of a method according to the present invention.

FIG. 3A shows a simplified flowchart of the method of measuring a thickness of a candidate tissue during a percutaneous myocardial revascularization procedure using a MR-OR catheter as described above. The method comprises positioning 31 a distal end of the catheter adjacent the candidate tissue; and measuring 34 the beginning thickness of the candidate tissue using optical reflectance, comprising either time-domain reflectance or optical coherence interferometry. Positioning 31 the MR-OR catheter typically entails placement of the distal end of the catheter adjacent a cardiac tissue which is a candidate tissue for revascularization by ablation. Positioning 31 can also include repositioning as tissue ablation proceeds. A myocardial revascularization procedure generally includes ablating 32 one or more channels in the candidate tissue and is ended 33 by the operator.

Figure 3B:
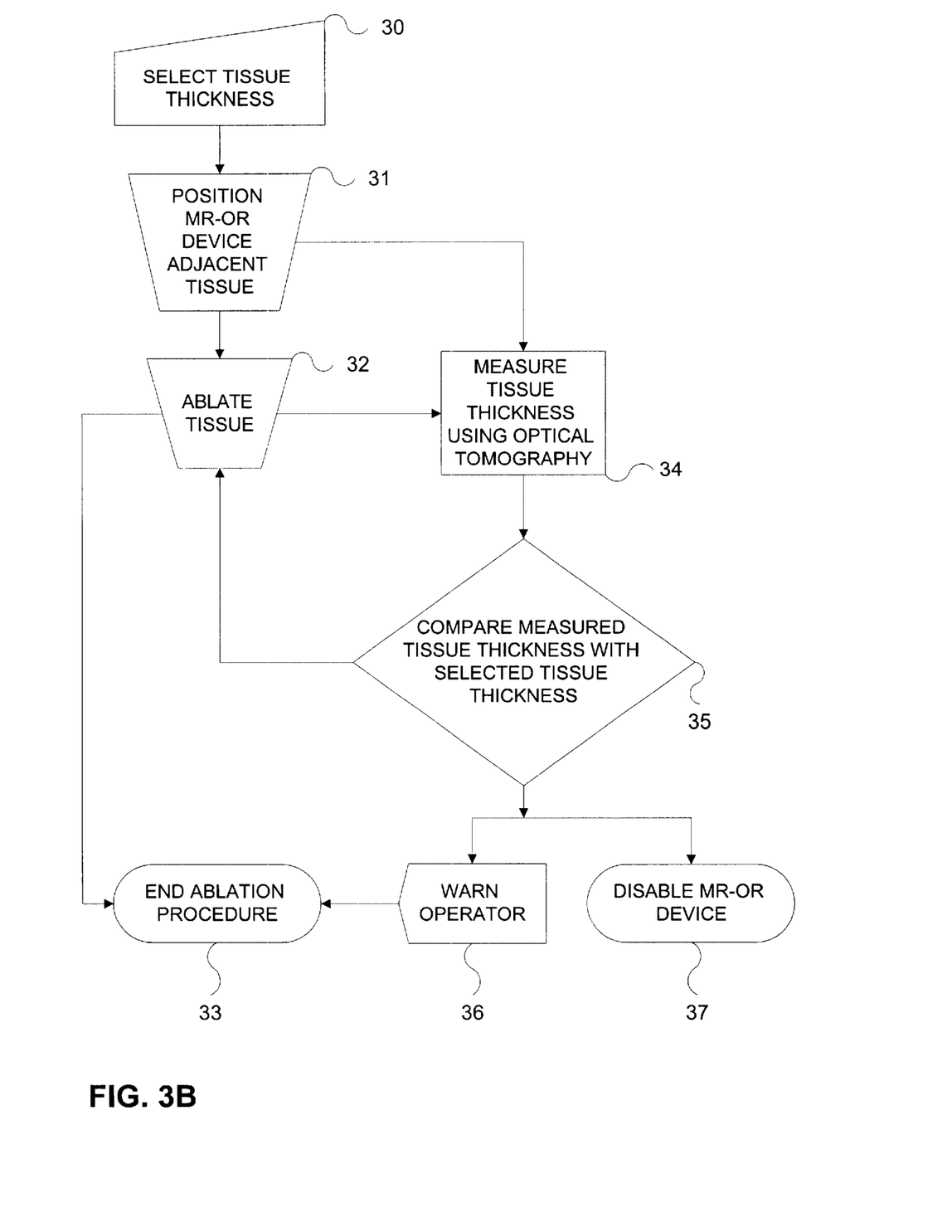
FIG. 3B is a flowchart of a preferred embodiment of the method shown in FIG. 3A.

In a preferred embodiment shown in FIG. 3B, the method further comprises selecting 30 a target tissue thickness before or during the myocardial revascularization procedure. After the catheter is positioned, the MR-OR device is operative to manually or automatically measure 34 a target tissue thickness. The measured tissue thickness is compared 35 to the target tissue thickness previously selected 30, enabling the MR-OR device to warn 36 an operator if a candidate tissue has a thickness of equal to or less than the selected target thickness. This warning permits the operator to end 33 the myocardial revascularization procedure or to identify another candidate tissue.

Tissue thickness can be measured at intervals or, alternatively, substantially continuously. Similarly, the MR-OR device can begin measuring tissue thickness as such tissue comes within measuring range of the device, or measurements can be postponed until later in the revascularization procedure, as desired.

The method can further comprise disabling 37 the tissue-ablating means of the MR-OR catheter when the measured 34 tissue thickness is equal to or less than the selected thickness to prevent further ablation of tissue not having more than the selected thickness. Disabling 37 the tissue-ablating means alleviates reliance on an operator to cease ablation when continued tissue ablation would be improvident, i.e., when the remaining tissue is so thin as to risk perforation by further ablation.

As shown in the embodiment in FIG. 3B, the method permits repeated cycling through the ablation-measurement-comparison loop (32-34-35) of the flowchart. The MR-OR device thereby permits unencumbered tissue ablation until detecting-via measuring and comparing-a candidate tissue possessing no more than the selected thickness, whereupon the tissue-ablating means is disabled to prevent potential tissue perforation.

In the method thus described, fluids can be introduced to the ablation site via the catheter or other device. For example, the site can be irrigated with saline or other fluid. This irrigation serves to prevent tissue adherence to the distal end of the catheter, where such tissue could potentially interfere with ablation or reflectance. A dye, e.g., radiographic dye, can be infused to the ablation site. Similarly, fluid and/or tissue fragments can be aspirated from the region adjacent the distal end of the catheter.

Figure 4A:
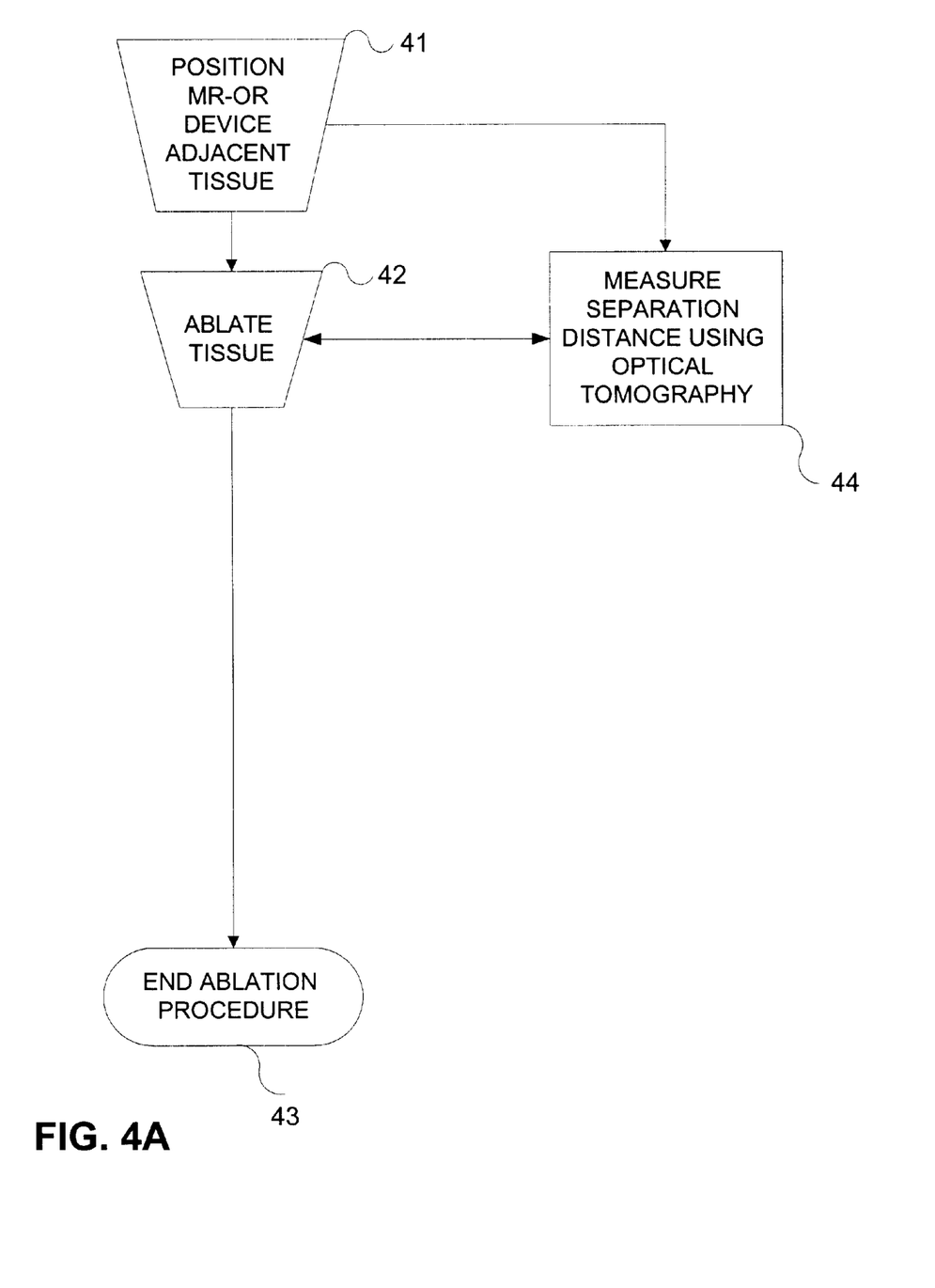
FIG. 4A is a flowchart of an alternative method according to the present invention.

FIG. 4A shows another aspect of the present invention, a method of determining a position of a MR-OR catheter relative to a boundary of a subject tissue in a myocardial revascularization procedure. This method comprises positioning 41 a distal end of the myocardial revascularization catheter adjacent to the subject tissue; and measuring 44 a separation distance from the distal end of the catheter relative to the boundary of the subject tissue using optical reflectance, comprising either time-domain reflectance or optical coherence interferometry. As explained above, a myocardial revascularization procedure generally includes ablating 42 tissue and is ended 43 by the operator. The method of FIG. 4A can be performed in conjunction with that of FIG. 3A, or separately.

Figure 4B:
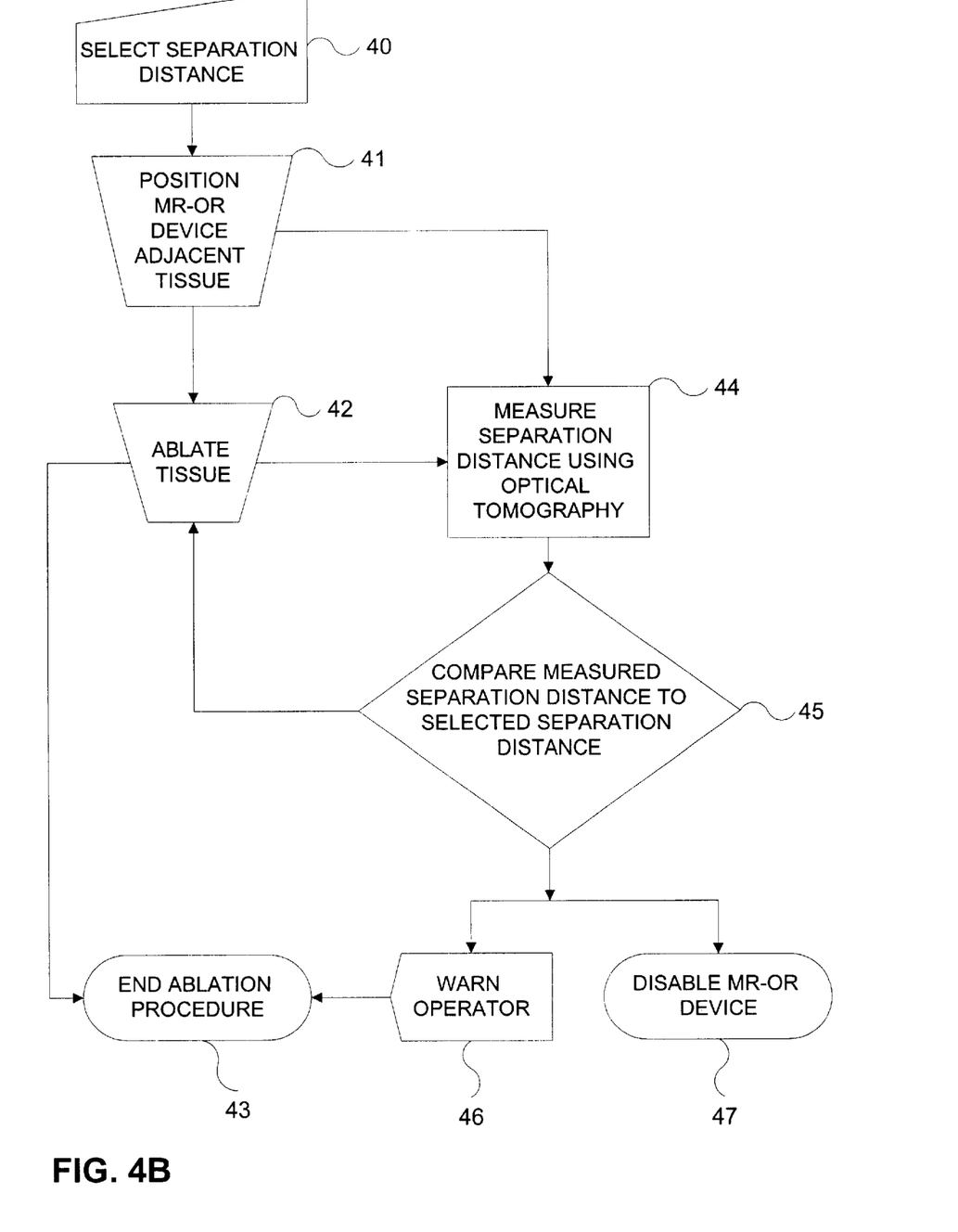
FIG. 4B is a flowchart of a preferred embodiment of the alternative method shown in FIG. 4A.

In a preferred embodiment shown in FIG. 4B, the method of determining a position of a MR-OR catheter relative to a boundary of a subject tissue in a myocardial revascularization procedure further comprises selecting 40 a separation distance, to which the measured separation distance can be compared 45. The MR-OR device can, in this embodiment of the method, be operated such that the operator is warned 46 when the selected separation distance meets or exceeds the measured separation distance or, alternatively, when the selected separation distance exceeds the measured separation distance.

This preferred method further comprises disabling 47 the tissue-ablating means to prevent further ablation of tissue when the distal end of the catheter is within a selected distance of the nearest tissue boundary, in order to prevent ablation of tissue not having more than the selected thickness. Such tissue boundary is typically the distal boundary of the tissue being ablated, such that the separation distance measured is the distance the catheter end would travel before perforating the tissue.

The preferred method permits repeated cycling through the ablation-measurement-comparison loop (42-44-45) of the flowchart in FIG. 4B. The MR-OR device thereby permits unencumbered tissue ablation until detecting-via measuring and comparing-that the distal end of the catheter is at or within a selected separation distance from a candidate tissue boundary, whereupon the tissue-ablating means is disabled to prevent potential tissue perforation.

The device of the present invention performs optical reflectance measurement by either time-domain reflectance or optical coherence interferometry. Time-domain reflectance systems employ ultra-short light pulse sources and measure the temporal response functions at various surface locations. The form and delay time of the temporal point spread function allows one to quantify the absorption and scattering properties of the trans-illuminated tissue in a spatially resolved manner, e.g., tissue imaging.

Optical coherence reflectance (OCR) employs a single mode fiber-optic Michelson white light interferometer. High-resolution cross-sectional imaging is achieved by focusing light from an optical low coherence source on the biological tissue and measuring the intensities of the back-scattered reflections as a function of their axial and transverse positions in the tissue. The light is scanned axially through the tissue by varying the reference arm path length. Intensity modulation associated with interference between light from the sample and reference arm reflections (heterodyning) occurs only when the optical path lengths of the two arms are matched to within the coherence length of the source. The intensity of back-scattered light is given by the amplitude of this heterodyned signal and plotted as a function of axial position in the sample.

Figure 5A:
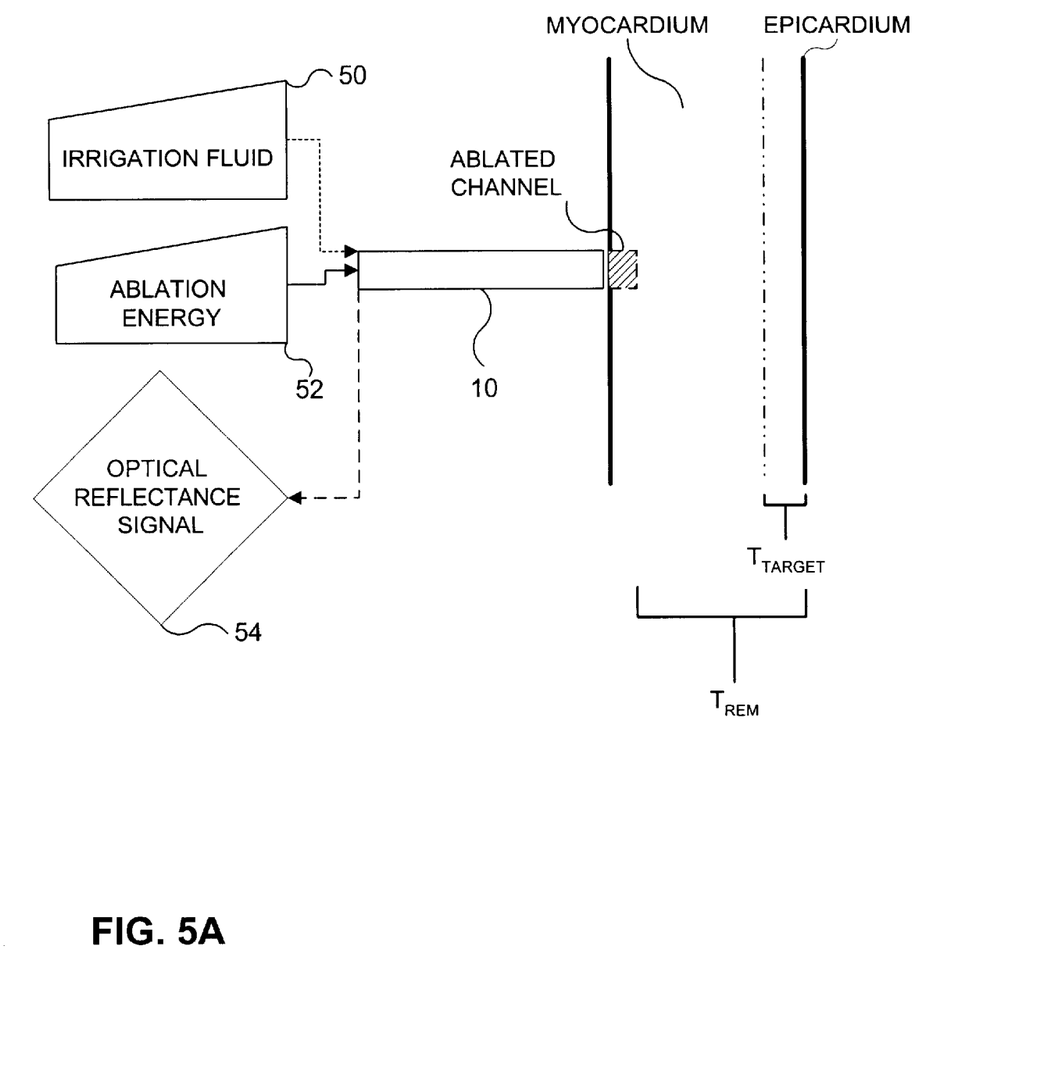
FIGS. 5A and 5B are diagrams of myocardial revascularization according to the method depicted in FIG. 3B, wherein the myocardial revascularization is in an early or late stage, respectively.

FIG. 5 is a diagram showing ablation of the myocardium using the MR-OR device according to the present invention. In FIG. 5A, the catheter has been positioned adjacent the myocardium and ablation begun by transmission of ablation energy 52 through the catheter 10 to the ablation site. Optical reflectance signals 54 are alternately or concomitantly received from the ablation site by way of the reflectance fiber. As mentioned, a fluid 50 can be introduced through the catheter to irrigate the ablation site.

Note that, as ablation is undertaken, the remaining tissue thickness $T_{REM}$ can be measured by the MR-OR device. The remaining tissue thickness $T_{REM}$ can also be compared to the selected tissue thickness $T_{TARGET}$.

Figure 5B:
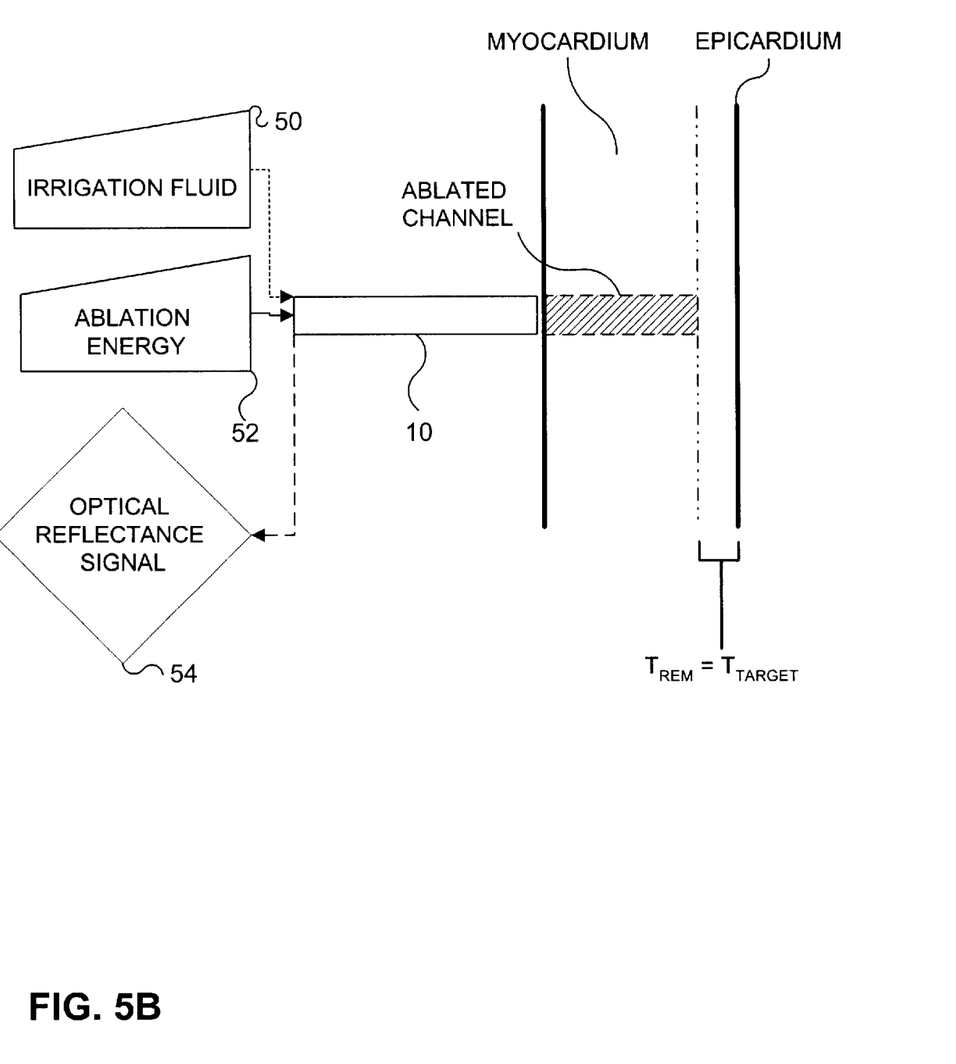

FIG. 5B shows the status of ablation when the remaining tissue thickness $T_{REM}$ is equal to the selected target tissue thickness $T_{TARGET}$. Such a condition triggers a warning 36 in one method according to the present invention. Alternatively or additionally, the ablation energy 52 can be interrupted or disabled 37, preventing further tissue ablation and the attendant risk of tissue perforation.

The method utilizing distance of separation from the catheter distal end to the distal tissue boundary can be used where a mechanical tissue-ablating means is employed, e.g., a rotary cutter. In such case, the catheter distal end will be advanced as ablation is performed. It should be clear that the device can readily measure 44 the distance from the catheter distal end to the most proximate distal boundary, and that it can further compare 45 such separation distance to a selected target separation distance. Where the catheter distal end reaches the target separation distance, a warning can be issued 46 and the tissue-ablating means can be disabled 47.

Using the previously described MR-OR device, a myocardial revascularization procedure was undertaken in vitro to ablate channels in the ventricular wall of a fresh porcine heart by laser ablation. The heart was bisected along its long axis to expose the left ventricular free wall and septum. A 60 μm diameter optical reflectance fiber was connected to an OCT device.

Figure 6:
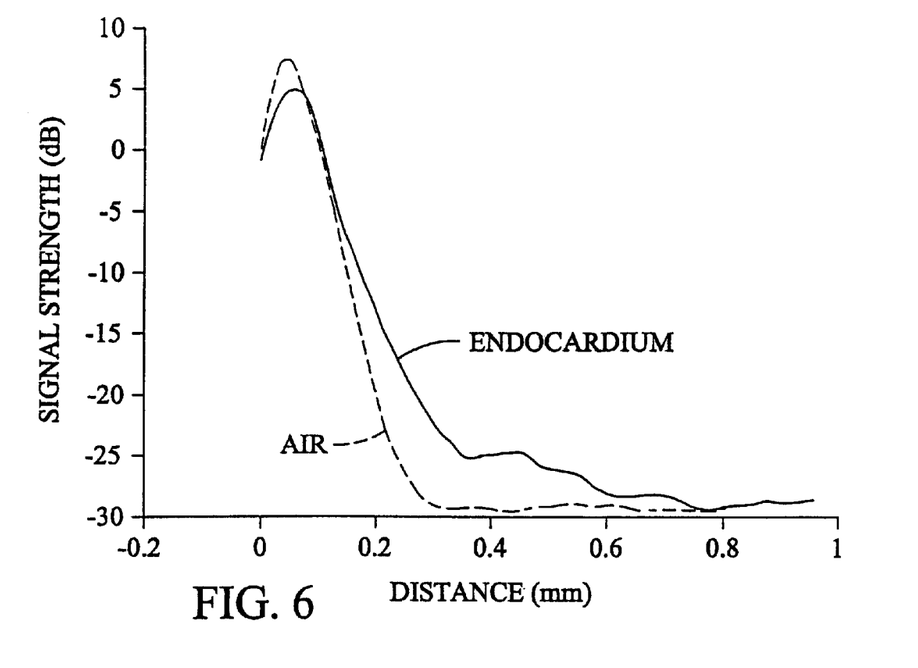
FIG. 6 is a graph of optical coherence reflectance (OCR) waveforms (representing air and endocardium) generated by one embodiment of the device according to the present invention.
Figure 7:
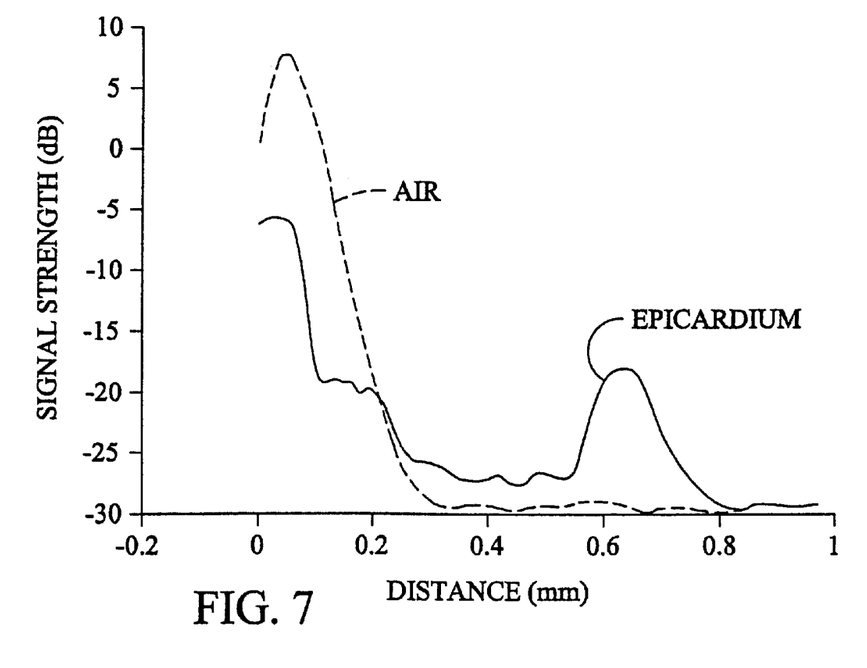
FIG. 7 is a graph of optical OCR waveforms (representing air and epicardium) similarly generated by the present invention.
Figure 8:
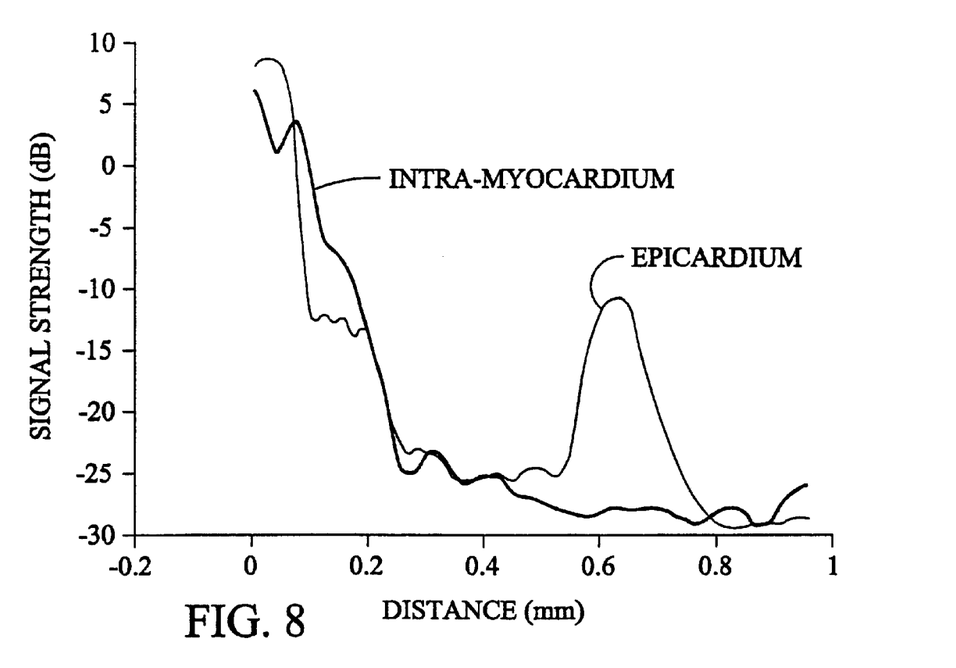
FIG. 8 shows OCR waveforms (representing intramyocardium and epicardium) generated by one embodiment of the device according to the present invention.
Figure 9:
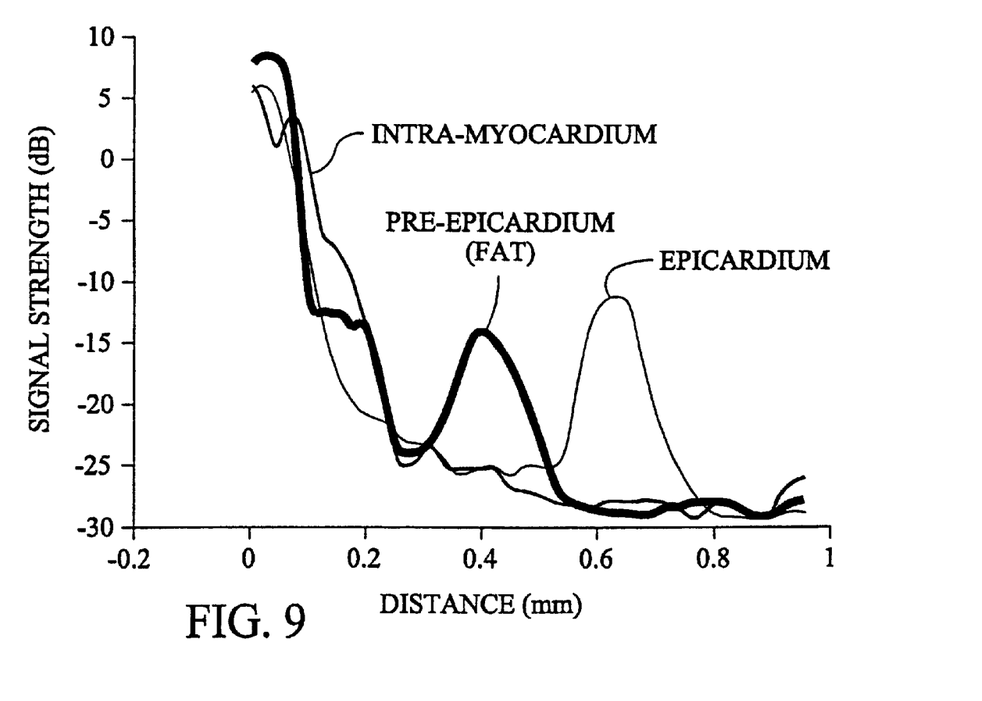
FIG. 9 shows OCR waveforms generated by one embodiment of the device according to the present invention (representing myocardium, epicardial fat, and epicardium).

Optical coherence reflectance signals were obtained, in air and under saline. The reflectance fiber was then positioned proximal to the inner surface of the heart (endocardium) and signals shown in FIG. 6 were obtained, both 1 mm from the surface and with the fiber in contact with the surface. The reflectance fiber was then inserted into the myocardium and intra-myocardial signals were obtained as the reflectance fiber was passed perpendicularly through the myocardium until it reached the outer surface of the heart (epicardium) with its visceral pericardium. The reflectance fiber could be seen tenting out the visceral portion of the epicardium inherently attached to the myocardium. Signals from the epicardium were obtained from the device in this orientation and are shown as a waveform in FIG. 7. The reflectance fiber was then allowed to perforate through the epicardial surface and signals were obtained as shown on FIG. 7 (air). Reflectance signals in FIGS. 6–9 clearly indicate the intra-myocardial, pre-epicardial and epicardial signals, all of which can be easily distinguished. The distance between the fiber tip and the epicardium is demonstrated.

Fresh porcine myocardium was obtained and bisected, exposing the endocardium, and submersed in a normal saline bath. The laser catheter was prepared such that the reflectance fiber was placed within the guidewire channel, positioned just at the distal end of the laser catheter, flush with the endhole, and secured so that a fixed location of the reflectance fiber tip was attained. An OCR sample in air was obtained, then the reflectance fiber tip was perpendicularly positioned against the endocardial surface and a second reflectance signal was obtained. The laser was activated at 50 mJ/mm2 at 25 Hz and advanced with minimal pressure. Continuous reflectance signals were obtained as the laser catheter vaporized through left ventricular free wall. When the reflectance fiber was located intra-myocardially, an optical reflectance signal differing from the endocardial signal was observed and no artifact of ultraviolet laser light was observed.

The signal changed as the tip of the reflectance fiber-equipped laser catheter approached the epicardial surface, a change consistent with a reflection from this surface. Verification of proximity to the epicardium was provided by visually detecting the red aiming beam of the laser catheter, which could be seen as the laser tip approached the epicardium. The distance from the laser catheter tip to the epicardium could be easily and precisely measured with the MR-OR device.

On some occasions, the laser was fired and the catheter intentionally advanced until it perforated the free wall of the myocardium-an event that was predicted well in advance by the reflectance signals. The operator observing the reflectance signal was otherwise unaware of the course of surgical events as the laser energy was applied and thus was blinded to the study except for the reflectance signal.

Because the light wavelengths used in laser ablation and optical reflectance are so disparate, interference between the optical ablation energy and the optical reflectance signals was not observed, nor was tissue thickness or catheter-tissue boundary separation distance gauging impaired.

In another study using six pigs, an 8-French guiding catheter was placed into the left ventricle. A 1.9 mm excimer laser angioplasty catheter was then introduced and positioned in the left ventricle. The laser catheter contained optical fibers circumferentially arranged around the central lumen. An OCR reflectance fiber was placed in the central lumen and positioned 1 mm beyond the end-hole in the distal portion of the laser catheter. This catheter was secured in place using an O-ring at the proximal end of the guiding catheter.

The guiding catheter was then placed fluoroscopically in the left ventricular apex, anterior and lateral wall of the heart flush against the endocardium.

The excimer laser catheter with the reflectance fiber was advanced as a unit while the laser was activated at 50 mJ in 25 Hz pulses. Continuous real-time OCR signals were monitored and used as the sole guide for channel depth. A total of sixty channels were produced in the six pigs. The channels penetrated to within 250 μm of the epicardium in every case.

The epicardium was identified in time to halt the laser ablation in 59 of the 60 channel ablations. In the one perforation instance, an epicardial signal was clearly observed but the spectrum was narrow-based. The operator performed another round of laser pulses, resulting in myocardial perforation and cardiac tamponade.

The animals were sacrificed after channel creation and the hearts retrieved for inspection. As discussed, only one perforation was observed. Angiograms of the channels, taken contemporaneous with the revascularization procedure, showed deep, well-formed channels that communicated with the endogenous vessels within the heart wall.

One of the seven pigs had similar instrumentation but with the reflectance fiber pulled back into the laser catheter approximately 30 cm so that it could not receive reflectance signals clearly. This misplacement of the reflectance fiber was done without the knowledge of the operator as a double-blind sham. The heart was quickly perforated in multiple areas as laser ablation was performed.

This study conclusively showed that OCR-guided myocardial revascularization can provide safe production of well-formed and therapeutic channels. Thus, a MR-OR laser catheter can accurately guide laser vaporization of myocardial channels so that impending perforation can be determined and avoided. By knowing the remaining depth of myocardium, the safety margin of TMR can be increased to allow creation of deeper channels. Deeper channels likely increase efficacy but are not currently employed due to fear of perforation, which can be life-threatening in percutaneous myocardial revascularization.

A person skilled in the art will be able to practice the present invention in view of the description present in this document, which is to be taken as a whole. Numerous details have been set forth in order to provide a more thorough understanding of the invention. In other instances, well-known features have not been described in detail in order not to obscure unnecessarily the invention.

While the invention has been disclosed in its preferred forms, the specific embodiments thereof as disclosed and illustrated herein are not to be considered in a limiting sense. Indeed, it should be readily apparent to those skilled in the art in view of the present description that the invention can be modified in numerous ways. The inventor regards the subject matter of the invention to include all combinations and subcombinations of the various elements, features, functions and/or properties disclosed herein.

What is claimed is:

1. A myocardial revascularization device, comprising:
    a catheter including:
        an elongate body having a proximal end and a distal end, and
        tissue-ablating means housed at least partially within the catheter and structured to emit an ablation signal suitable to ablate tissue adjacent the distal end of the catheter, said ablation signal including energy selected from the group consisting of optical ablation energy having an optical ablation energy wavelength, acoustical ablation energy, and radiofrequency ablation energy;
    an optical reflectance fiber housed within the catheter, said fiber coupled to an optical reflectance system, said reflectance fiber structured to output an optical reflectance signal generated from said optical reflectance system;
    wherein the device is operative to gauge a tissue thickness from a first tissue boundary to a second tissue boundary by receiving a reflected optical reflectance signal in the optical reflectance fiber and wherein the optical reflectance signal comprises either short optical pulses or low-coherence light having a wavelength different from the optical ablation energy wavelength.

2. The myocardial revascularization device of claim 1, further comprising means for signaling an operator when a remaining tissue thickness of a tissue adjacent the distal end of the catheter is equal to or less than a selected thickness after ablation from the first tissue boundary toward the second tissue boundary.

3. The myocardial revascularization device of claim 1, further comprising means for disabling the tissue-ablating means when a remaining tissue thickness of a tissue adjacent the distal end of the catheter is equal to or less than a selected thickness after ablation from the first tissue boundary toward the second tissue boundary.

4. The myocardial revascularization device of claim 1, further comprising means for signaling an operator when a distance from the distal end of the catheter to the second tissue boundary is equal to or less than a selected distance.

5. The myocardial revascularization device of claim 1, further comprising means for disabling the tissue-ablating means when the distance from the distal end of to catheter to the second tissue boundary is equal to or less than a selected distance.

6. The myocardial revascularization device of claim 1, wherein the optical reflectance system includes a low-coherence light source comprising a super-luminescent light-emitting diode.

7. The myocardial revascularization device of claim 6, wherein the super-luminescent light-emitting diode produces light having a wavelength in the range of 900 nm to 1400 nm.

8. The myocardial revascularization device of claim 1, wherein the tissue-ablating means comprises an optic fiber housed at least partially within the catheter and coupled to a laser energy generating source.

9. The myocardial revascularization device of claim 8, wherein the laser energy generating source generates laser energy pulses and optical reflectance signals transmitted by the optical reflectance system are interleaved with the laser energy pulses.

10. The myocardial revascularization device of claim 8, wherein the tissue-ablating means comprises a plurality of optic fibers housed at least partially within the catheter and coupled to a laser energy generating source.

11. The myocardial revascularization device of claim 10, wherein the reflectance fiber and the plurality of optic fibers are circumferentially ranged within the catheter.

12. The myocardial revascularization device of claim 10, wherein the catheter further comprises an internal lumen, the plurality of optic fibers are circumferentially arranged in the catheter and the reflectance fiber is removably positioned in said internal lumen.

13. The myocardial revascularization device of claim 1, wherein an optic fiber is housed within the catheter, said optic fiber being capable of transmitting laser energy to ablate tissue adjacent the distal end of the catheter.

14. The myocardial revascularization device of claim 13, wherein the laser energy is pulsed and optical reflectance signals transmitted along the optical fiber are interleaved with the laser energy pulses.

15. The myocardial revascularization device of claim 1 wherein the optical reflectance signal source is a low-coherence light source comprising a super-luminescent light-emitting diode.

16. The myocardial revascularization device of claim 15 wherein the super-luminescent light-emitting diode produces light having a wavelength in the range of 900–1400 nm.

* * * * *

UNITED STATES PATENT AND TRADEMARK OFFICE
CERTIFICATE OF CORRECTION

PATENT NO.     : 6,660,001 B2
DATED          : December 9, 2003
INVENTOR(S)    : Gregory

It is certified that error appears in the above-identified patent and that said Letters Patent is hereby corrected as shown below:

Column 5,
Line 29, "means 14 comprises" should read -- means comprises --.
Line 30, "source coupled" should read -- source 14 coupled --.
Line 66, "means 14 removably" should read -- means removably --.

Column 6,
Line 2, "means 14 can be" should read -- means can be --.
Line 4, "means 14 can reside" should read -- means can reside --.

Signed and Sealed this

Twentieth Day of July, 2004

JON W. DUDAS
*Acting Director of the United States Patent and Trademark Office*